United States Patent
Golan

(10) Patent No.: US 10,143,481 B2
(45) Date of Patent: Dec. 4, 2018

(54) STABILIZER ASSEMBLY FOR FRACTURING CALCIFICATIONS IN HEART VALVES

(71) Applicant: PI-CARDIA LTD., Rehovot (IL)

(72) Inventor: Erez Golan, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 236 days.

(21) Appl. No.: 14/759,228

(22) PCT Filed: Jan. 5, 2014

(86) PCT No.: PCT/US2014/010265
§ 371 (c)(1),
(2) Date: Jul. 5, 2015

(87) PCT Pub. No.: WO2014/107633
PCT Pub. Date: Jul. 10, 2014

(65) Prior Publication Data
US 2015/0335340 A1    Nov. 26, 2015

Related U.S. Application Data

(60) Provisional application No. 61/749,440, filed on Jan. 7, 2013.

(51) Int. Cl.
*A61B 17/00* (2006.01)
*A61B 17/221* (2006.01)
(Continued)

(52) U.S. Cl.
CPC ...... *A61B 17/221* (2013.01); *A61B 17/00234* (2013.01); *A61B 17/3207* (2013.01); *A61B 2017/00243* (2013.01); *A61B 2017/00292* (2013.01); *A61B 2017/2212* (2013.01); *A61B 2017/22098* (2013.01)

(58) Field of Classification Search
CPC ............ A61B 17/00234; A61B 17/221; A61B 17/3207; A61B 2017/00243
See application file for complete search history.

(56) References Cited

U.S. PATENT DOCUMENTS 9,554,816 B2 * 1/2017 Golan ................ A61B 17/22
2007/0038293 A1 2/2007 St Goar Frederick
(Continued)

FOREIGN PATENT DOCUMENTS

DE   102010011773   9/2011
WO   2011/069025   6/2011

OTHER PUBLICATIONS

PCT Search Report PCT/US2014/010265, dated Apr. 2, 2014.

*Primary Examiner* — Julie A Szpira
(74) *Attorney, Agent, or Firm* — Dekel Patent Ltd.; David Klein

(57) ABSTRACT

A device for fracturing calcifications in heart valves includes a stabilizer assembly (20) for use with an impactor assembly (10). Relative motion between the impactor assembly (10) and the stabilizer assembly (20) with sufficient energy fractures a calcification located in tissue which is sandwiched between the stabilizer assembly (20) and the impactor assembly (10). The stabilizer assembly (20) includes a plurality of distal stabilizer struts (28) connected by stabilizer loops (30) which extend proximally backwards.

6 Claims, 2 Drawing Sheets

(51) Int. Cl.
    A61B 17/3207    (2006.01)
    A61B 17/22      (2006.01)

(56)         References Cited

U.S. PATENT DOCUMENTS

2008/0033467 A1*  2/2008  Miyamoto ............. A61B 17/22
                                                      606/180
2008/0058765 A1*  3/2008  Jais ...................... A61B 5/0422
                                                      604/523
2010/0076408 A1*  3/2010  Krever ............. A61B 17/00234
                                                      604/529
2012/0022633 A1   1/2012  Olson

* cited by examiner

STABILIZER ASSEMBLY FOR FRACTURING CALCIFICATIONS IN HEART VALVES

CROSS-REFERENCE TO RELATED APPLICATIONS

This application is a national phase application of PCT patent application PCT/US2014/010265, filed 5 Jan. 2014, which claims priority under 35 USC § 119 to U.S. Provisional Patent Application, Ser. No. 61/749440, filed Jan. 7, 2013, which are incorporated herein by reference.

FIELD OF THE INVENTION

The present invention generally relates to devices and methods for fracturing calcifications in heart valves, such as aortic valve leaflets.

BACKGROUND OF THE INVENTION

PCT Patent Application PCT/US2012/067812 describes devices and methods that may be used for fracturing calcifications in aortic valve leaflets, in order to increase leaflet pliability and mobility, either as standalone treatment, bridge treatment or preparation of the "landing zone" for trans-catheter valve implantation. In addition, the devices and methods described can be applied as a preparation step for trans-catheter aortic valve implantation, in order to allow valve implantation in heavily calcified or asymmetrically calcified native valves, to increase the cross-sectional area of the implanted valve and to decrease the risk of paravalvular leaks. The devices and methods may also be used for fracturing calcifications in other valves, such as the mitral valve, for performing angioplasty on calcified plaque, or for fracturing hard deposits such as kidney or bladder stones.

SUMMARY OF THE INVENTION

The present invention seeks to provide further devices for fracturing calcifications in aortic valve leaflets, as is described further below.

The term "fracture" refers to any kind of reduction in size or any modification in shape or form, such as but not limited to, fracturing, pulverizing, breaking, grinding, chopping and the like.

There is provided in accordance with an embodiment of the invention a device for fracturing calcifications in heart valves including a stabilizer assembly for use with an impactor assembly, wherein relative motion between the impactor assembly and the stabilizer assembly with sufficient energy fractures a calcification located in tissue which is sandwiched between the stabilizer assembly and the impactor assembly, wherein the stabilizer assembly includes a plurality of distal stabilizer struts connected by stabilizer loops which extend proximally backwards.

In accordance with an embodiment of the invention the stabilizer assembly includes a shaft from which extend a plurality of arms which include the stabilizer struts at distal portions thereof.

In accordance with an embodiment of the invention distal portions of the arms include a bridge section, distally from which extend the stabilizer struts.

In accordance with an embodiment of the invention the bridge sections are wider than the stabilizer struts.

In accordance with an embodiment of the invention the stabilizer struts are curved.

In accordance with an embodiment of the invention a sheath is provided in which the stabilizer assembly is initially stored.

There is also provided in accordance with an embodiment of the invention a method for fracturing calcifications in heart valves including causing relative motion between an impactor assembly and a stabilizer assembly with sufficient energy so as to fracture a calcification located in tissue which is sandwiched between the stabilizer assembly and the impactor assembly, wherein the stabilizer assembly includes a plurality of distal stabilizer struts connected by stabilizer loops which extend proximally backwards.

BRIEF DESCRIPTION OF THE DRAWINGS

The present invention will be understood and appreciated more fully from the following detailed description, taken in conjunction with the drawings in which:

FIGS. 2A-2C are simplified illustrations of a stabilizer for use with an impactor (such as, but not limited to, the impactor of FIG. 1), constructed and operative in accordance with an embodiment of the invention, wherein FIG. 2A shows loops of the stabilizer at the beginning of deployment from a sheath, FIG. 2B shows further deployment with the stabilizer partially open, and FIG. 2C shows full deployment of the stabilizer.

DETAILED DESCRIPTION OF EMBODIMENTS

Figure 1:
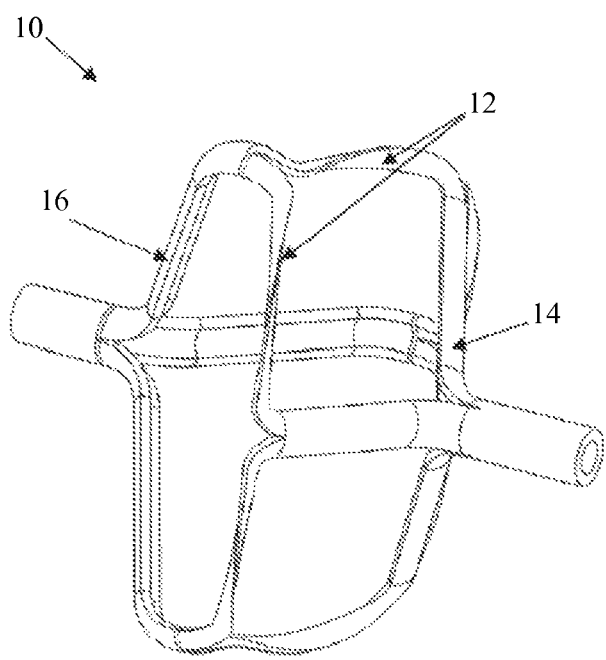
FIG. 1 is a simplified illustration of a "stent-like" impactor of the prior art, described in PCT Patent Application PCT/US2012/067812.

Reference is now made to FIG. 1, which illustrates an impactor assembly 10 of the prior art, described in PCT Patent Application PCT/US2012/067812. Impactor assembly 10 includes one or more impaction struts 12, which extend between proximal structural struts 14 and distal structural struts 16. The "stent-like" impactor preferably, but not necessarily, contacts the leaflets from their ventricular aspect using impaction struts 12. Impaction struts 12 run along the connection of the leaflet to the aortic wall, creating a footprint on an area that, if not because of calcific deposits, would be flexible enough to allow high mobility of the leaflets. The positions of distal structural struts 16 are illustrated at about 120° apart, but this is non-limiting. Fractures along or near the footprint of the "stent-like" impactor results in a significant increase in aortic valve cross sectional area during systole. The "stent-like" impactor may be used in various rotational positions on the valve, preferably, but not necessarily, with proximal structural struts 14 on the ventricular aspect of the commissures, which is the "natural" rotational position of the impactor. Alternatively, the impactor can be rotated so that the proximal structural struts contact the centerline of the valve's leaflets.

Figure 2A:
Figure 2B:
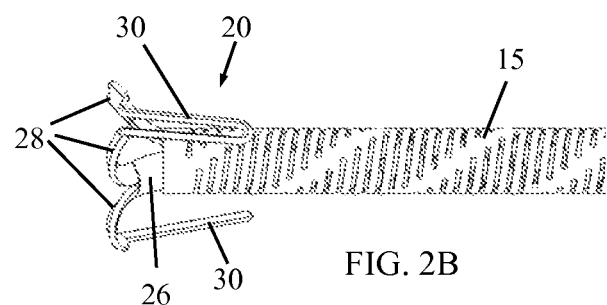
Figure 2C:
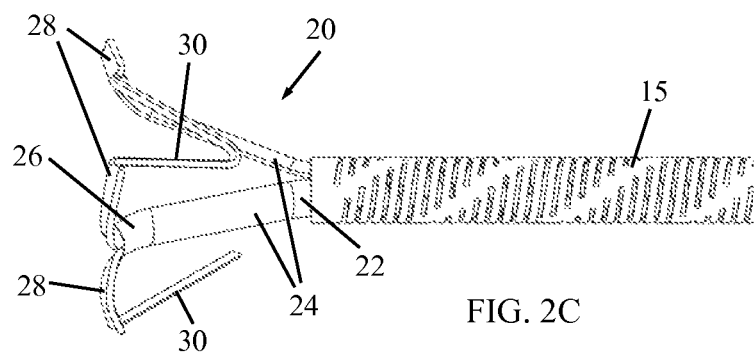

Reference is now made to FIGS. 2A-2C, which illustrate a stabilizer assembly 20, in accordance with an embodiment of the invention. Stabilizer assembly 20 may be deployed from an external sheath 15, which may be flexible, such as by means of a pattern of staggered or phase-shifted notches or cuts (e.g., laser cuts) formed along the axial length of the sheath.

Stabilizer assembly 20 may include a shaft 22, from which extend a plurality of arms 24 (e.g., three, spaced 120° apart). Distal portions of arms 24 include a relatively wide bridge section 26, distally from each of which there extend a pair of curved, relatively narrow stabilizer struts 28. The stabilizer struts 28 of neighboring arms 24 are connected by stabilizer loops 30, which extend proximally backwards towards shaft 22.

FIGS. 2A-2C show the progression of the deployment of assembly 20. FIG. 2A shows loops 30 at the beginning of deployment from sheath 15. FIG. 2B shows further deployment with the stabilizer partially open, and FIG. 2C shows full deployment of the stabilizer. Shaft 22 is shown in FIG. 2C still in sheath 15 but it is normally completely removed upon use. Alternatively, for some particular situations, shaft 22 may remain partially in sheath 15 during usage.

Stabilizer assembly 20 preferably, but not necessarily, contacts the leaflets from their aortic aspect using bridge sections 26 and struts 28. Struts 28 may be positioned on the bases of the leaflets so as to counteract the impactor (such as impactor 10 of FIG. 1) in order to break calcific deposits mainly along the base of the leaflet (its connection to the aortic wall). The bridge sections 26 may be positioned on the centerline of the leaflets in order to break calcific deposits mainly along the central folding line of the leaflets.

Stabilizer assembly 20 can be positioned in various rotational positions on the valve, preferably, but not necessarily, with its bridge sections 26 along the centerline of the leaflet or with its bridge sections 26 on the commissures so that each strut 28 is touching two leaflets at a time.

Stabilizer loops 30 help protect the valve and aortic wall from possible injury from the tips of stabilizer struts 28. The shape of the loops 30 facing upwards (proximally) allows them to go over the valve commissures, so that the stabilizer struts 28 contact the leaflets, and also helps in attaining proper angular orientation of stabilizer assembly 20.

What is claimed is:

1. A device for fracturing calcifications in heart valves comprising:

a stabilizer assembly for use with an impactor assembly, wherein relative motion between said impactor assembly and said stabilizer assembly with sufficient energy fractures a calcification located in tissue which is sandwiched between said stabilizer assembly and said impactor assembly, wherein said stabilizer assembly comprises a shaft from which extend a plurality of arms and wherein a pair of distal stabilizer struts extend, in different directions from each other from distal portions said arms;

and further comprising stabilizer loops, each of said loops comprising a pair of legs connected to each other at a proximal end of the loop to form a curved, closed proximal end and distal ends of the legs being spaced from each other, wherein one of said distal ends of said legs is coupled to a first one of said distal stabilizer struts and the other one of said distal ends of said legs is coupled to a second one of said distal stabilizer struts adjacent to said first one of said distal stabilizer struts, said curved, closed proximal end being proximal to said distal ends of said legs.

2. The device according to claim 1, wherein distal portions of said arms comprise bridge sections, distally from which extend said stabilizer struts.

3. The device according to claim 2, wherein said bridge sections are wider than said stabilizer struts.

4. The device according to claim 1, wherein said stabilizer struts are curved.

5. The device according to claim 1, further comprising a sheath in which said stabilizer assembly is initially stored.

6. The device according to claim 5, wherein said stabilizer loops extend proximally backwards towards an end of said sheath.

* * * * *